United States Patent [19]
Ram et al.

[11] Patent Number: 6,136,992
[45] Date of Patent: Oct. 24, 2000

[54] 2-ALKOXY ESTRADIOLS AND DERIVATIVES THEREOF

[75] Inventors: Siya Ram, Winchester, Mass.; Ravi Varma, Rockville, Md.; Yesh Sachdeva, Concord, Mass.

[73] Assignees: The United States of America as represented by the Department of Health and Human Services, Washington, D.C.; Pharm-Eco Laboratories, Incorporated, Lexington, Mass.

[21] Appl. No.: 09/041,212

[22] Filed: Mar. 12, 1998

Related U.S. Application Data

[60] Provisional application No. 60/040,540, Mar. 13, 1997.
[51] Int. Cl.$^7$ .................................. C07J 1/00; C07J 41/00
[52] U.S. Cl. ........................ 552/614; 552/518; 552/519; 552/522
[58] Field of Search .................................. 552/518, 519, 552/522, 614

[56] References Cited

U.S. PATENT DOCUMENTS 5,521,168   5/1996   Clark ........................................ 514/178

OTHER PUBLICATIONS

Berg et al., "Synthesis of immunogenic C–6 derivatives of 2–methoxyestrone and 2–methoxyestradiol–17.beta. and characterization of the corresponding antisera". Hoppe–Seyler's Z. Physiol. Chem., vol. 363, pp. 737–744, 1982.

Cushman et al., "Synthesis, antitubulin and antimitotic activity, and cytotoxicity of analogs of 2–methoxyestradiol, an endogenous mammalian metabolite of estradiol that inhibits tubulin polymerization by binding to the colchicine binding site." J. Med., 1995.

Breuer, H. and Knuppen, R., "Biosynthesis of 2–Methoxyestradiol Human Liver," *Naturwissenschaften* 12:280–281 (1960). (Translatic enclosed).

Gelbke, H.P. and Knuppen, R., "The Excretion of Five Different 2–Hydroxyestrogen Monomethyl Ethers in Human Pregnancy Urine," *J. Steroid Biochem.* 7:457–463 (1976).

Seegers, J.C., et al., "The Cytotoxic Effects of Estradiol–17β, Catecholestradiols and Methoxyestradiols on Dividing MCF–7 and HeLa Cells," *J. steroid Biochem.* 32(6):797–809 (1989).

Cushman, M., et al., "Synthesis, Antitubulin and Antimitotic Activity, and Cytotoxicity of Analogs of 2–Methoxyestradiol, an Endogenous Mammalian Metabolite of Estradiol that Inhibits Tubulin Polymerization by Binding to the Colchicine Binding Site," *J. Med. Chem.* 38:2041–2049 (1995).

D'Amato, R.J., et al., "2–Methoxyestradiol, an endogenous mammalian metabolite, inhibits tubulin polymerization by interacting at the colchicine site," *Proc. Natl. Acad. Sci. USA* 91:3964–3968 (1994).

Hamel, E., et al., "Interactions of 2–Methoxyestradiol, an Endogenous Mammalian Metabolite, with Unpolymerized Tubulin and with Tubulin Polymers," *Biochemistry* 35:1304–1310 (1996).

Fotsis, T., et al., "The endogenous oestrogen metabolite 2–methoxyoestradiol inhibits angiogenesis and suppresses tumour growth," *Nature* 368:237–239 (1994).

Klauber, N., et al., "Inhibition of Angiogenesis and Breast Cancer in Mice by the Microtubule Inhibitors 2–Methoxyestradiol and Taxol," *Cancer Res.* 57:81–86 (1997).

Folkman, J., et al., "Induction of angiogenesis during the transition from hyperplasia to neoplasia," *Nature* 339:58–61 (1989).

Blood, C.H. and Zetter, B.R., "Tumor Interaction with the Vasculature: Angiogenesis and Tumor Metastasis," *Biochim. Biophys. Acta* 1032:89–118 (1990).

He, H–M and Cushman, M., "Versatile Synthesis of 2–Methoxyestradiol, an Endogenous Metabolite of Estradiol which Inhibits Tubulin Polymerization by Binding to the Colchicine Binding Site," *Bioorg. Med. Chem. Lett.* 4(14):1725–1728 (1994).

Castro, C.E., et al., "Indoles, Benzofurans, Phthalides, and Tolanes via Copper(i) Acetylides," *J. Org. Chem.* 31:4071–4078 (1966).

Sonogashira, K., et al., "A Convenient Synthesis of Acetylenes: Catalytic Substitution of Acetylenic Hydrogen with Bromoalkenes, Iodoarenes, and Bromopyridines," *Tetrahedron Lett.*:4467–4470 (1975).

Nicolaou, K.C., et al., "Total Synthesis of Novel Geometric Isomers of Lipoxin $A_4$ and Lipoxin $B_4$," *J. Org. Chem.* 54:5527–5535 (1989).

Watanabe, M. et al., "A Facile Synthesis of Benzo [b] furan Derivatives Including Naturally Occurring Neolignans via Regioselective Lithiation of ortho–Cresols Using Bis(dimethylamino)phosphoryl Group as a Directing Group," *Chem. Pharm. Bull.* 39(1):41–48 (1991).

(List continued on next page.)

*Primary Examiner*—Barbara Badio
*Attorney, Agent, or Firm*—Hamilton, Brook, Smith & Reynolds, P.C.

[57] ABSTRACT

Compounds represented by the following structural formula:

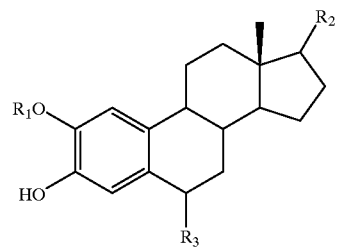

wherein $R_1$, $R_2$ and $R_3$ are as defined in the specification. The compounds are disclosed as useful in the treatment of various forms of cancer.

3 Claims, 3 Drawing Sheets

OTHER PUBLICATIONS

Aitken, A. and Burns, G., "Flash Vacuum Pyrolysis of Stabilised Phosphorus Ylides. Part 3. Preparation of o–Methoxyphenyl– and o–Methylsulfanylphenyl–alkynes and their Cyclisation to Benzofurans and Benzothiophenes," *J. Chem. Soc., Perkin Trans.* 2455–2460 (1994).

Baldwin, J.E., "Rules for Ring Closure," *J. Chem. Soc., Chem. Commun.*:734–736 (1976).

Buckle, D.R. and Rockell, C.J.M., "A Versatile Two–Stage Synthesis of 2–Substituted Benzo[b] furans from (2–Methoxyphenyl)ethynes," *J. Chem. Soc., Perkin Trans. 1*:2443–2446 (1985).

Manecke, G. and Zerpner, D., "Synthesis of Substituted 2–Arylbenzofurans," *Chem. Ber. 105*:1943–1948 (1972).

Castro, C.E. and Stephens, R.D., "Substitutions by Ligands of Low Valent Transition Metals. A Preparation of Tolanes and Heterocyclics from Aryl Iodides and Cuprous Acetylides," *J. Org. Chem. 28*:2163 (1963).

Stephens, R.D. and Castro, C.E., "The Substitution of Aryl Iodides with Curpous Acetylides. A Synthesis of Tolanes and Heterocycles," *J. Org. Chem. 28*:3313–3315 (1963).

Irurre, J. Jr., et al., "Inhibition of Rat Liver Microsomal Lipid Peroxidation Elicited by 2,2–Dimethylchromenes and Chromans Containing Fluorinated Moieties Resistant to Cytochrome P–450 Metabolism," *Bioorg. Med. Chem. 1*(3):219–225 (1993).

Baker, M.H., et al., "Effect of ω–trifluorination on the microsomal metabolism of ethyl and pent–1–yl p–nitrophenyl ether," *Xenobiotica 16*(3):195–203 (1986).

McQuinn, R.L., et al., "Biotransformation and Elimination of $^{14}$C–Flecainide Acetate in Humans," *Drug Metab. Dispos. 12*(14):414–420 (1984).

Fuji, K., et al., "Hard Acid and Soft Nucleophile System. New Efficient Method for Removal of Benzyl Protecting Group," *J. Org. Chem. 44*(10):1661–1664 (1979).

Hamacher, H. and Christ, E., "Potential Antineoplastics. 7th Comm.: Introduction of a Nitrogen Mustard Group into the 6α–Position of Estradiol," *Arzneim–Forsch./Drug Res. 33(I)*:347–352 (1983).

Dean, P.D.G., et al., "Preparation of 17β–Oestradiol–6–(O–Carboxymethyl) Oxime Bovine Serum Conjugate," *Steroids 18*:593–603 (1971).

Leeds, J.P. and Kirst, H.A., "A Mild Single–Step Reduction of Oximes to Amines," *Syn. Comm. 18*:777–782 (1988).

Hoffman, C., et al., "Synthesis of α–Amino Acids by Reduction of α–Oximino Esters with Titanium(III) Chloride and Sodium Borohydride," *J. Org. Chem. 54*:3750 (1989).

Hirami, Y., et al., "Synthesis and Antimicrobial Activity of Som Steroidal Amines," *Agric. Biol. Chem. 39*:843–850 (1975).

Shoppee, C.W. and Sly, J.C.P., "Steroids and Walden Inversion. Part XLI. The Deamination of Some A–Nor–, B–Nor, and 17–Amino–steroids," *J. Chem. Soc.*:345–356 (1959).

Boyd, M.R. and Paull, K.D., "Some Practical Considerations and Applications of the National Cancer Institute In Vitro Anticance Drug Discovery Screen," *Drug Development Res. 34*:91–109 (1995).

Slaunwhite, J., W.R. and Neely, L., "Bromination of Phenolic Steroids. I. Substitution of Estrone and 17β–Estradiol in Ring A," *J. Org. Chem. 27*:1749–1752 (1962).

Schwenk, E., et al., "Halogenation of Estrone and Derivatives," *J. Org. Chem. 28*:136–144 (1963).

Hamel, E. and Lin, C.M., "Separation of Active Tubulin and Microtubule–Associated Proteins by Ultracentrifugation and Isolation of a Component Causing the Formation of Microtubule Bundles," *Biochemistry 23*:4173–4184 (1984).

Katzenellenbogen, J.A., et al., "Photoaffinity Labels for Estrogen Binding Proteins of Rat Uterus," *Biochemistry 12*(21):4085–4092 (1973).

2-ALKOXY ESTRADIOLS AND DERIVATIVES THEREOF

RELATED APPLICATIONS

This application claims the benefit of U.S. Provisional Application, U.S. Ser. No. 60/040,540, filed Mar. 13, 1997, the entire teachings of which are incorporated herein by reference.

GOVEREMENT FUNDING

This invention was made with government support under National Cancer Institute Contract No. NOI-CM-27764. The government has certain rights in the invention.

BACKGROUND OF THE INVENTION

At least some 2-alkoxy-estra-3,17β-diols (hereinafter "2-alkoxy estradiols") have anticancer activity. For example, when tested in mice, 2-methoxy estradiol (1) acts as a potent inhibitor of neovascularization of solid tumors and inhibits their growth at doses which produce no apparent signs of toxicity (Fotsis et al., *Nature* 368:237 (1994). 2-Methoxy estradiol (1) is thought to inhibit tumor growth act by: 1) inhibiting DNA synthesis and mitosis (Breuer et al., *Naturwissenschaft* 12:280 (1960) and Gelbke et al., *J. Steroid Biochem*, 7:457 (1976) ); 2) inhibiting tubulin polymerization or causing the formation of tubulin polymer with altered morphology and stability properties (D'Amato et al., *Proc. Natl. Acad. Sci. U.S.A.*

(1)

91:3964 (1994)); or 3) inhibiting angiogenesis, i.e. the creation of new blood vessels required for the growth of solid tumors (Fotsis et al., *Nature* 368:237 (1994), Folkman et al., *Nature* 339:58 (1994) and Blood et al., *Biochim. Biophys. Acts* et al., 1032:89 (1990)).

2-Alkoxy estradiols are estrogen analogs and are therefore expected to have affinity for the estrogen receptor. This could complicate their use as anticaner agents. Thus, there is also a need for new 2-alkoxy estradiols and analogs thereof with improved activity compared with 2-methoxy estradiol (1) and with reduced affinity for the estrogen receptor.

SUMMARY OF THE INVENTION

The present invention is directed to novel 2-alkoxy estradiols and derivatives of 2-alkoxy estradiols having anticancer activity. The invention is also directed to methods of preparing these novel compounds.

One embodiment of the present invention is a compound represented by the following structural formula:

$R_1$ is a C1–C6 lower alkyl group or substituted lower alkyl group. Preferably, $R_1$ is ethyl or 2,2,2-trifluoroethyl.

$R_2$ is —OH or —$NH_2$. Preferably $R_2$ is —OH and has the beta configuration.

$R_3$ is selected from the group consisting of =O, —H, =N—$NH_2$, =N—NH—$SO_2$-(lower alkyl), =N—NH—$SO_2$-(substituted lower alkyl), =N—NH—$SO_2$-phenyl, =N—NH—$SO_2$-(substituted phenyl), =N—OH, =N—O-(lower alkyl) and =N—O-(substituted lower alkyl). However, $R_3$ is not —H or =O if $R_1$ is methyl and $R_2$ is —OH. $R_3$ is preferably =N—OH, =N—O-(lower alkyl) and =N—O(substituted lower alkyl). More preferably, $R_3$ is =N—OH or =N—O—$CH_3$.

Another embodiment of the present invention is the compound 2-ethoxy estra-3,17β-diol (2) or 2-(2',2',2'-trifluoroethoxy)estra-3,17β-diol (3).

Another embodiment is a method of treating an individual with cancer. The method comprises administering to the individual a therapeutically effective amount of a compound represented by the following structural formula:

$R_1$, $R_2$ and $R_3$ are as described above.

Another embodiment of the present invention is a method of treating an individual with cancer by administering a therapeutically effective amount of 2-ethoxy estradiol (2) or 2-(2',2',2'-trifluoroethoxy)estra-3,17β-diol (3).

The disclosed novel compounds have improved activity against a wide variety of tumor cells lines, including lung, colon, central nervous system, melenoma, ovarian, renal, prostate and breast, compared with 2-methoxy estradiol (1). Therefore, it is expected that they will be useful in the treatment of a wide variety of cancers. In addition, they have low affinity for the estrogen receptor and are therefore expected to have fewer side effects than 2-methoxy estradiol (1).

DETAILED DESCRIPTION OF THE INVENTION

The features and details of the invention will now be more particularly described below and pointed out in the claims. It will be understood that the particular embodiments of the invention are shown by way of illustration and not as limitations of the invention. The principal features of this invention can be employed in various embodiments without departing from the scope of the invention.

2-Alkoxy estradiols and a numbering system for identifying each carbon atom in the estradiol ring system are shown in the following structural formula:

$R_1$ is a lower alkyl group or a substituted lower alkyl group.

As used herein, suitable lower alkyl groups include C1–C6 straight or branched chain hydrocarbons which can optionally contain one or more double or triple bonds.

Suitable substitutents on a lower alkyl group or phenyl group include one or more halogens (e.g., fluoro, chloro, bromo and iodo), nitro, nitrile, —$NH_2$, —NH(lower alkyl), —NH (substituted lower alkyl), —N(lower alkyl)$_2$, —N(substituted lower alkyl)$_2$, carbonyl groups, —$CONH_2$, —CONH(lower alkyl), —CONH(substituted lower alkyl), —CON(lower alkyl)$_2$, —CON(substituted lower alkyl)$_2$, —$CO_2H$, —COO(lower alkyl) and —COO(substituted lower alkyl). Halogenated alkyl groups can contain more than one kind of halogen. Examples of suitable lower alkyl or substituted lower alkyl groups include methyl, ethyl, n-propyl, isopropyl, trifluoromethyl, trifluoroethyl, $NO_2$—$CH_2$—$CH_2$—, $(CH_3)_2N$—$CH_2$—$CH_2$—, —$CH_2CH_2$—CO—R', wherein R' is —H, lower alkyl, substituted lower alkyl, —OH, —O lower alkyl), —O(substituted lower alkyl), —$NH_2$, —NH(lower alkyl), —NH (substituted lower alkyl), —N(substituted lower alkyl)$_2$ and —N(lower alkyl)$_2$.

Figure 1:
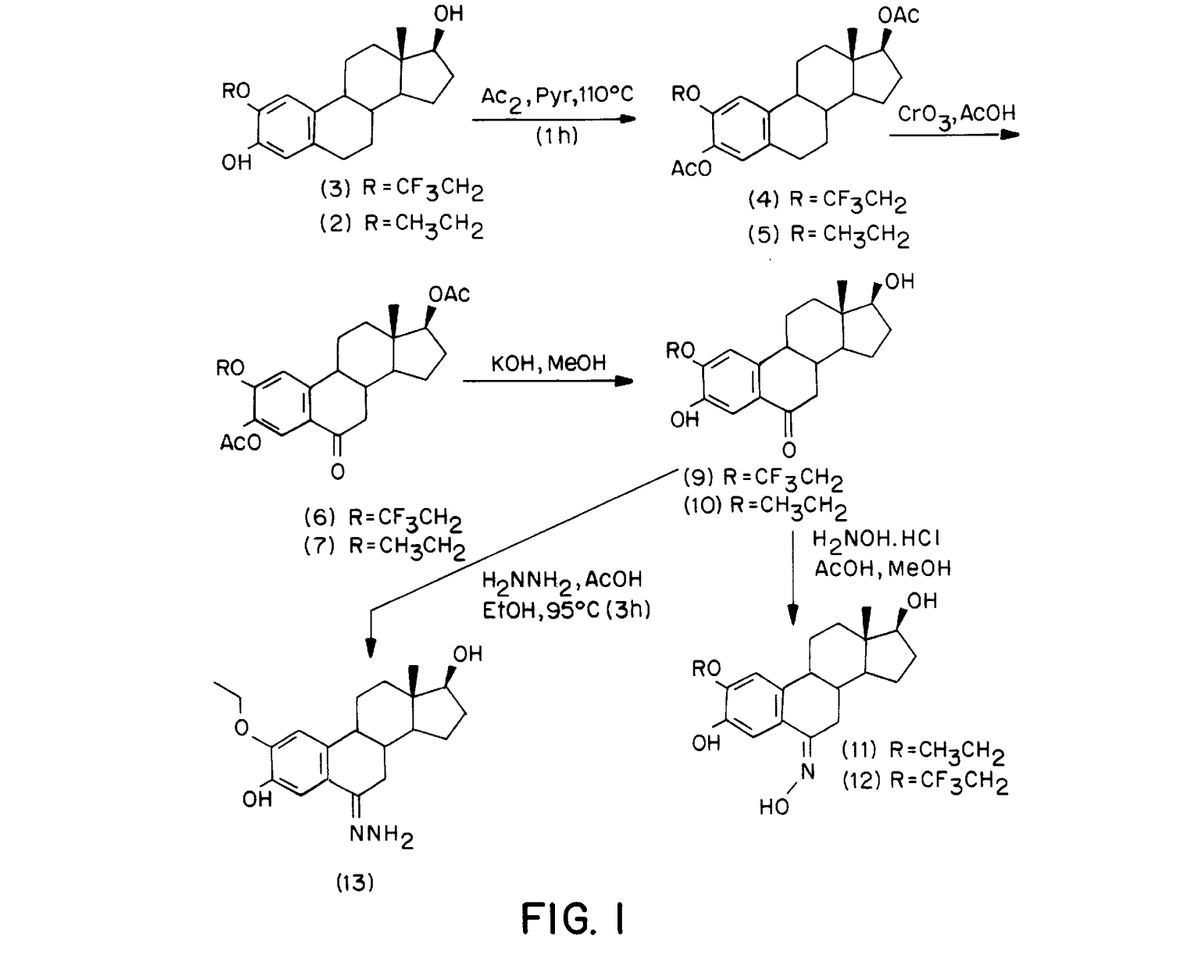
FIG. 1 is a schematic showing the synthesis of 2-alkoxy estradiols substituted at the six position with =N—OH and =$NNH_2$ from 2-ethoxy estradiol (2) and 2-(2',2',2'-trifluoroethoxy) estradiol (3).
Figure 2:
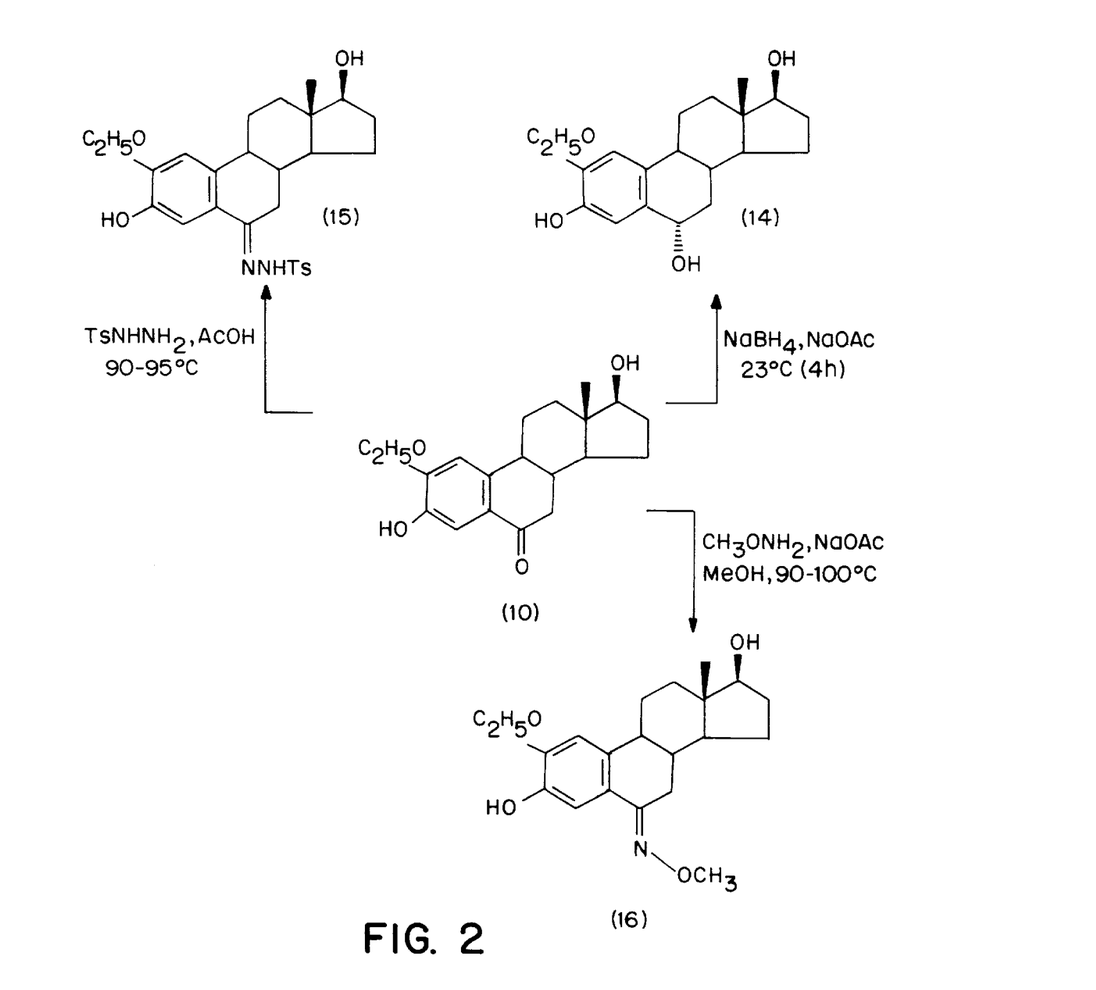
FIG. 2 is a schematic showing the synthesis of 2-ethoxy estra-1,3,5(10)-triene-3,6α,17β-triol (14) and 2-ethoxy estra-1,3,5(10)-triene-3,17β-diol-6-tosylhydrazone (15) from 2-ethoxy estradiol (2).
Figure 3:
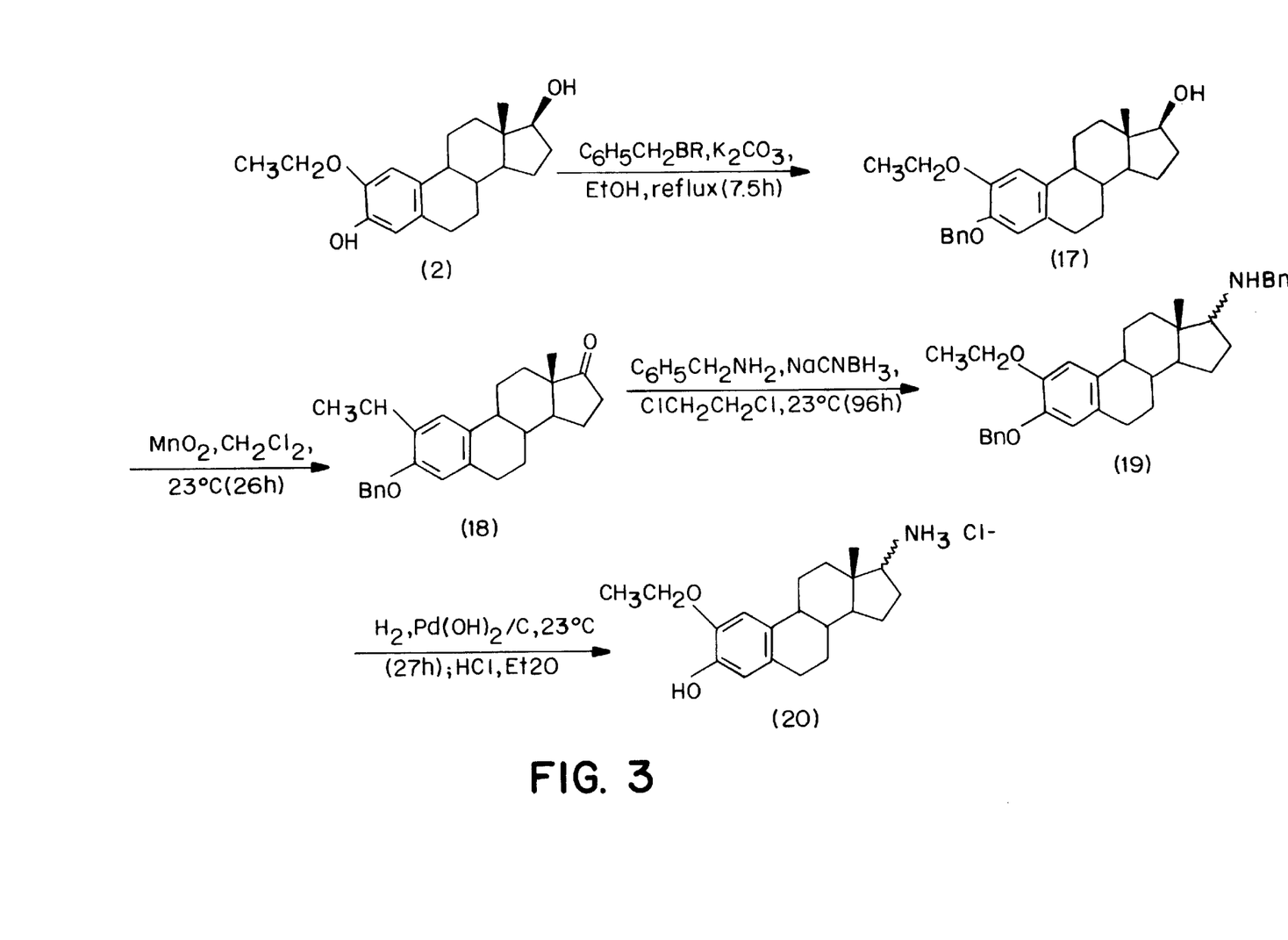
FIG. 3 is a schematic showing the synthesis of 2-ethoxy-3-hydroxy-17-aminoestra-1,3,5(10)-triene (20) from 2-ethoxy estradiol (2).

The compounds of the present invention can be prepared using 3,17-diprotected 2-alkoxy estradiols as starting materials. 2-Alkoxy estradiols can be prepared, for example, by methods disclosed in Cushman et al., *J. Med. Chem.* 38:2041 (1995) and in co-pending U.S. patent application entitled "Improved Synthesis of 2-Alkoxy Estradiols", filed on Mar. 13, 1997 (Ser. No. 08/816,558), the entire teachings of which are incorporated. herein by reference. The reactions used to prepare the compounds of the present invention from 2-alkoxy estradiols are shown in FIGS. I–III and are described in greater detail hereinbelow.

A first intermediate represented by Structural Formula (I) is prepared from a 2-alkoxy estradiol by protecting the two hydroxyl groups:

$R_1$ is as described above. $R_4$ and $R_5$ are hydroxyl protecting groups and may be the same or different. As used herein, hydroxyl refers to alcohols and phenolic groups. A "suitable protecting group" is substantially inert with respect to the reagents used in the subsequent reactions in the disclosed synthesis of 2-alkoxy estradiols and does not cause, for example, undesired side reactions. Hydroxyl protecting groups are well known in the art and are described in, for example, Chapters 2 and 3 of Greene and Wuts, "Protective Groups in Organic Synthesis", John Wiley & Sons (1991), the entire teachings of which are incorporated into this application by reference. The skilled artisan can select, using no more than routine experimentation, suitable groups for use in the disclosed synthesis as well as conditions for applying and removing the hydroxyl protecting groups.

Preferred hydroxyl protecting groups are acyl groups. The term "acyl group" includes, for example, is —CO-(lower alkyl) or —CO-(substituted lower alkyl). Preferred acyl groups are acetyl groups. Methods of acylating free hydroxyl groups are known in the art and are disclosed in Chapter Three (pages 87–103) and Chapter Six (pages 162–169) of Greene and Wuts, the teachings of which are incorporated herein by reference. Examples of specific conditions for acylating 2-alkoxy estradiols, specifically estradiol (2) and estradiol (3), are provided in Examples 1 and 2.

The six position of the first intermediate is oxidized to a ketone to form a second intermediate represented by Structural Formula (II):

$R_1$, $R_4$ and $R_5$ are as described above.

Suitable conditions for preparing a compound represented by Structural Formula (II) from a compound represented by Structural Formula (I) include performing the reaction, for example, at temperatures of from about 0° C. about 35° C., preferably from about 5° C. to about 15° C. with an excess of $CrO_3$, for example from about a two fold to about an eight fold excess, preferably about a four to five fold excess. Suitable concentrations of estradiol range from, for example, 0.05 M to about 5.0 M in acetic acid. Specific conditions for oxidizing the six position of a 2-alkoxy estradiol, specifically estradiols (4) and (5), to the corresponding ketones (6) and (7), respectively, are provided in Examples 4 and 3. The hydroxyl protecting groups in the second intermediate are deprotected to form a third intermediate represented by Structural Formula (III):

(III)

$R_1$ is as defined above. Suitable conditions for removal of the hydroxyl protecting are disclosed in Chapters 2 and 3 of Green and Wuts and references cited therein, as described above. Specific conditions for deprotecting estradiols (6) and (7) are provided in Examples 6 and 5, respectively.

A compound represented by Structural Formula (III) can be converted to the corresponding hydrazone by reaction with the appropriate hydrazine, $NH_2$—$NHR_6$, or to the corresponding hydroxylimine or alkoxylimine by reaction with hydroxylamine or the corresponding alkoxylamine, $NH_2$—$OR_7$. These products are represented by Structural Formula (IV).

(IV)

$R_6$ is selected from the group consisting of —H, —$SO_2$-(lower alkyl), —$SO_2$ (substituted lower alkyl) —$SO_2$-phenyl and —$SO_2$ (substituted phenyl).

$R_7$ is selected from the group consisting of —H, lower alkyl and substituted lower alkyl. $R_7$ is preferably —H or —$CH_3$.

Methods of converting a ketone to a hydrazone, hydroxyl amine or alkoxylamine are well known in the field of organic chemistry and disclosed, for example, on pages 804–06 of March and in references cited therein, the teachings of which are incorporated herein by reference. Specific conditions for the preparation of hydrazone (13), hydroxylimine (11), hydroxylimine (12), methoxylimine (16) and tosylhydrazone (15) are provided in Examples 9, 7, 8, 12 and 11, respectively.

A compound represented by Formula (III) can be converted to a compound represented by Structural Formula (V) by a ketone reducing agent. Suitable ketone reducing (V)

agents include hydride reducing agents, such as sodium borohydride, lithium borohydride and lithium aluminum hydride and borane reducing reagents such as diborane. Conditions for carrying out the reduction of a ketone to an alcohol with ketone reducing reagents are well known in the field of organic chemistry and are disclosed in for example, in Brown et al., *Aldrichimica Acta* 12:3 (1979) and references cited therein, the teachings of which are incorporated herein by reference. Specific conditions for carrying out the reduction of ketone (10) to alcohol (14) are provided in Example 10.

2-Alkoxy estradiols can be used in a four step synthesis of a compound represented by Structural Formula (VI):

(VI)

$R_1$ is as defined above.

The phenolic group at position three of a 2-alkoxy estradiol is selectively protected, preferably selectively benzylated to form a first intermediate represented by Structural Formula (VII):

(VII)

$R_1$ is as described above. $R_8$ is a phenolic protecting group, preferably a benzyl or substutited benzyl group. Hydroxyl groups can be benzylated by reacting at least one equivalent of a benzyl chloride, bromide or iodide and at least one equivalent of a base per free hydroxyl group (see, for example, Venuti et al., *J. Med. Chem.* 31:2132 (1988)). Because phenolic groups are more basic than alcohols, the phenolic group can be selectively benzylated. in the presence of the alcohol at position seventeen by using a weak base such as $K_2CO_3$ or NaOH. The reaction is preferably monitored by, for example, thin layer chromatography. A catalytic amount of an iodide salt can be added to the reaction mixture, e.g., NaI, KI or tetraalkylammonium iodide. Examples of suitable substituents on a benzyl protecting group include, but are not limited to, one or more of the following groups: lower alkyl, fluoro, chloro, (lower alkyl)-O—, nitro, phenyl, di(lower alkyl)aminocarbonyl and silyl. As used herein "benzylating" refers to protecting a free hydroxyl group (alcohol or phenolic group) with a benzyl group or substituted benzyl group. Specific conditions for selectively benzylating the phenolic group of estradiol (10) are provided in Examples 13 and 14.

The first intermediate represented by Structural Formula (VII) is reacted with a reagent suitable for oxidizing secondary alcohols to ketones to form a compound represented by Structural Formula (VIII):

(VIII)

$R_1$ and $R_8$ are as described above.

Reagents for oxidizing second alcohols to ketones and conditions for carrying out the reaction are well known in the field of organic chemistry and are disclosed, for example, in March on pages 1057–60 and references cited therein, the teachings of which are incorporated herein by reference. Suitable reagents include, for example, pyridinium dichromate (PDC), pyridinium chloro chromate (PCC and $MnO_2$. Specific conditions for oxidizing 3-protected 2-alkoxy estradiol (17) to the corresponding ketone (18) with $MnO_2$ are provided in Example 14.

The ketone group in the second intermediated represented by Structural Formula (VIII) is reductively aminated with $NH_2$—$R_{10}$ and an imine reducing agent to form a compound represented by Structural Formula (IX):

(IX)

$R_1$ and $R_8$ are as described above. $R_{10}$ is —H or an amine protecting group, for example benzyl or substituted benzyl. Suitable reagents, e.g. imine reducing agents and conditions for performing a reductive amination on a ketone group are well known in the art and are disclosed, for example, on pages 796–998 of March and in Lane, *Sodium Cyanoborohydride: A Highly Selective Reducing Agent*, "Selections From Aldrichimica Acta" Aldrich Chemical Co., page 67–78 (1984), and references cited therein, the teachings of which are incorporated herein by reference. Specific conditions for reductively aminating ketone (18) are provided in Example 15.

The phenolic group at position three and the amine group are deprotected in the compound represented by Structural Formula (IX) to form a compound represented by Structural Formula (VI). As discussed above, suitable conditions for deprotecting a phenolic group are well known in the field of organic chemistry and examples are provided in Chapter Three of Greene and Wuts. Suitable conditions for deprotecting an amine group, including a benzyl protecting group, are provided in Chapter Seven of Greene of Wuts and references cited therein, the teachings of which are incorporated herein by reference. Specific conditions for deprotecting amine (19) are provided in Example 16.

An "individual" is preferably a human, but can also be animals in need of treatment, e.g., veterinary animals (e.g., dogs, cats, and the like), farm animals (e.g., cows, pigs, horses and the like) and laboratory animals (e.g., rats, mice, guinea pigs and the like).

A "therapeutically effective amount" is the quantity of compound which results in an improved clinical outcome as a result of the treatment compared with a typical clinical outcome in the absence of the treatment. An "improved clinical outcome" includes a longer life expectancy. It can also include slowing or arresting the rate of growth of a tumor, causing a shrinkage in the size of the tumor or a decreased rate of metastasis.

The amount of compound administered to the individual will depend on the type and severity of the disease and on the characteristics of the individual, such as general health, age, sex, body weight and tolerance to drugs. The skilled artisan will be able to determine appropriate dosages depending on these and other factors. Typically, a therapeutically effective amount of the compound can range from about 1 mg per day to about 1000 mg per day for an adult. Preferably, the dosage ranges from about 1 mg per day to about 100 mg per day.

The compound can be administered orally, for example, in capsules, suspensions or tablets or by parenteral administration. Parenteral administration can include, for example, systemic administration, such as by intramuscular, intravenous, subcutaneous, or intraperitoneal injection.

The compound can be administered to the individual in conjunction with an acceptable pharmaceutical carrier as part of a pharmaceutical composition for treating cancer, inflammatory disease, or the other diseases discussed above. Suitable pharmaceutical carriers may contain inert ingredients which do not interact with the compound. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The invention is illustrated by the following examples which are not intended to be limiting in any way.

EXEMPLIFICATION

Melting points were determined in capillary tubes on a Mel-Temp apparatus and are uncorrected. Spectra were obtained as follows: CI mass spectra on a Finnegan 4000 spectrometer; FAB mass spectra and EI mass spectra on a Krat:os MS50 spectrometer; $^1$H NMR spectra on a Bruker AC 300 spectrometer; IR spectra on a Beckman IR-33 spectrophotometer or a Nicolet FT-IR Impact 410 spectrophotometer. Microanalyses were performed by MicroAtlantic Laboratories, Atlanta, and all values were within ±0.4% of the calculated compositions.

EXAMPLE 1

2-Ethoxy-3,17β-Diacetyloxyestra-1,3,5(10)-Triene (5)

Acetic anhydride (1.7 mL, 18 mmol) was added dropwise under an argon atmosphere at 0° C. to a solution of 2-ethoxy estra-1,3,5(10)-trien-3,17β-diol (2) (0.44 g, 1.4 mmol) in anhydrous pyridine (6 mL). The resulting mixture was stirred at 110° C. for 1 h. The reaction mixture was cooled to room temperature and poured onto ice cold 3 N HCl (50 mL). The compound was extracted with ethyl acetate (150 ML×2). The combined organic layer was washed with water (80 mL), sodium bicarbonate (100 mL), water (80 mL), brine 100 mL), and dried over anhydrous sodium sulfate. The ethyl acetate layer, on evaporation under reduced pressure, gave estradiol (5) (0.50 g, 90%): mp 135–136° C.; $R_f$ 0.66 [hexane-ethyl acetate (7:3), silica gel]; IR (KBr) 2970–2860, 1765, 1725, 1505, 920, 885 $cm^{-1}$; $^1H$ NMR ($CDCl_3$) δ 0.87 (s, 3 H), 1.15–2.00 (m, 13 H), 2.10 (s, 3 H), 2.12–2.38 (m, 3 H), 2.35 (s, 3 H), 2.70–2.90 (m, 2 H), 4.05 (q, J=6.4 Hz, 2 H), 4.71 (t, J=8.5 Hz, 1 H), 6.75 (s, 1 H), 6.9 (s, 1 H). Anal. ($C_{24}H_{32}F_3O_5$) C, H.

EXAMPLE 2

2-(2',2',2'-Trifluoroethoxy)-3-17β-Diacetyloxy-Estra-1,3,5(10)-Triene (4)

Acetic anhydride (10 mL) was added dropwise under an argon atmosphere at 0° C. to a solution of 2-trifluoroethoxyestra-1,3,5(10)-trien-3,17β-diol (3) (2.50 g, 6.7 mmol) in anhydrous pyridine (20 mL). The resulting mixture was stirred at 110° C. for 1 h. The reaction mixture was cooled to room temperature and poured onto ice-cold 3 N HCl (100 mL). The compound was extracted into ether (2×250 mL). The combined organic layer was washed with water (60 mL), sodium bicarbonate (60 mL), water (60 mL), brine (80 mL), and dried over anhydrous magnesium sulfate. The ether layer, on evaporation under reduced pressure, gave an almost quantitative yield (2.5 g) of estradiol (4). An analytical sample was prepared by purification by column chromatography (silica gel using hexane-ethyl acetate (8:2)): mp 116–118° C.; $R_f$ 0.63 [hexane-ethyl acetate (8:2), silica gel]; IR (KBr) 2960–2840, 1755, 1705, 1490, 950 $cm^{-1}$; $^1H$ NMR ($CDCl_3$) δ 0.85 (S, 3 H), 1.15–2.00 (m, 10 H), 2.05 (S, 3 H), 2.15–2.40 (m, 6 H), 2.70–2.90 (m, 2 H), 4.30 (q, J=8.5 Hz, 2 H), 4.70 (t, J=8.5 Hz, 1 H). 6.80 (s, 1 H), 6.95 (s, 1 H). Anal. ($C_{24}H_{29}F_3O_5$) C, H.

EXAMPLE 3

2-Ethoxy-3,17β-Diacetoxy-6-Oxoestra-1,3,5(10)-triene (7)

A solution of chromium trioxide (1.6 g, 16 mmol) in 90% glacial acetic acid (7.5 mL) was added dropwise at 15° C. to a solution of 2-ethoxy-3,17β-diacetyl derivative (5), (1.5 g, 3.7 mmol) in glacial acetic acid (12 mL). The resulting mixture was stirred at 15° C. for 35 min. The mixiure was poured onto ice-water mixture (150 mL) and compound was extracted into ethyl acetate (3×180 mL). The combined organic layer was washed with water (100 mL), $NaHCO_3$ solution (100 mL), water (100 mL), brine (100 mL), and dried over anhydrous sodium sulfate. The organic layer, upon evaporation under reduced pressure, provided a crude compound, which on purification on a silica gel column using hexane: ethyl acetate mixture aas eluant gave 1.20 g (55%) of estradiol (7): mp 195° C.; IR (KBr) 2980–2810, 1765, 1730, 1715, 1665, 1600, 1500, 918, 880 $cm^{-1}$; $^1H$ NMR ($CDCl_3$) δ 0.89 (s, 3 H), 1.30–1.85 (m, 9 H), 1.90–2.45 (m, 11 H), 2.47–2.85 (m, 2 H), 4.15 (q, J=6.4 Hz, 2 H), 4.78 (t, J=8.5 Hz, 1 H), 6.95 (s, 1 H), 7.77 (s, 1 H). Anal. ($C_{24}H_{30}O_6$) C, H.

EXAMPLE 4

2-(2',2',2'-Trifluoroethoxy)-3,17β-Diacetyloxy-Estra-6-Oxo-1,3,5(10)-Triene (6)

A solution of chromium trioxide (2.0 g, 20 mmol) in 90% glacial acetic acid (10 mL) was added dropwise at 9–10° C. to a solution of 2-trifluoroethoxy-3,17β-O-diacetyl estradiol (4)(2.1 g, 4.6 mmol) in glacial acetic acid (14 mL). The resulting mixture was stirred at 10° C. for 60 min. After completion, the mixture was poured onto ice-water mixture (150 mL) and compound was extracted into ethyl acetate (3×200 mL). The combined organic layer was washed with water (100 mL), $NaHCO_3$, solution (100 mL), water (100 mL), brine (100 mL), and dried over anhydrous sodium sulfate. The organic layer, on evaporation under reduced pressure, provided a residue, which on purification over a silica gel column using hexane:ethyl acetate mixture as eluant gave the desired estradioil (6) (1.35 g, 61%): mp 131–133° C.; $R_f$ 0.59 [hexane-ethyl acetate (7:3), silica gel]; IR (KBr) 2960–2840, 1770, 1730, 1675, 1610, 1500, 890, 850 $cm^{-1}$; $^1H$ NMR ($CDCl_3$) δ 0.83 (s, 3 H), 2.83–1.27 (m, 19 H), 4.45 (q, J=8.5 Hz, 2 H), 4.75 (t, J=8.5 Hz, 1 H), 6.93 (s, 1 H), 7.80 (s, 1 H). Anal. ($C_{24}H_{27}O_6$) C, H.

EXAMPLE 5

2-Ethoxy-6-Oxoestra-1,3,5(10)-Triene-3,17β-Diol (10)

A 20% solution of KOH in methanol (5 mL) was added drcpwise to a suspension of estradiol (7) (0.95 g, 2.3 mmol) in anhydrous methanol (12 mL). The resulting reaction mixture was stirred at room temperature for 4 h. The solvent was removed under reduced pressure at 42–45° C. The residue was diluted with ice-water mixture (30 mL), and extracted with ethyl acetate (3×125 mL). The combined organic layer was washed with ice-cold water (30 mL), brine (30 mL) and dried over anhydrous sodium sulfite. The organic layer, on evaporation under vacuum, gave estradiol (10) (0.7 g, 92%). An analytical sample was prepared by a short column chromatography on silica gel using EtOAc, followed by EtOAc—MeOH (18:1), and finally chloroform: mp 194–196° C.; IR (KBr) 3400–3200, 2960–2842, 1650, 1590, 1500, 890, 852 $cm^{-1}$; $^1H$ NMR ($DMSO$-$d_6$+$D_2O$) δ 0.85 (s, 3 H), 1.20–1.80 (m, 10 H), 1.82–2.82 (m, 8 H), 3.72 (t, J=8.5 Hz, 1 H), 4.20 (q, J=6.4 Hz, 2 H), 6.85 (s, 1 H), 7.58 (s, 1 H). Anal. ($C_{20}H_{26}O_4$) C, H.

EXAMPLE 6

(2',2',2'-Trifluoroethoxy)-6-Oxo-2-Estra-1,3,5(10)-Triene-3,17β-Diol (9)

A 20% solution of KOH in methanol (7 mL) was added dropwise to a suspension of estradiol (6) (1.1 gm 2.4 mmol) in anhydrous methanol (20 mL). The resulting reaction mixture was stirred at room temperature for 5 h. The solvent was removed under reduced pressure at 42–45° C. The residue was neutralized with ice-cold 3N HCl, and the solid that separated was isolated by filtration. This solid was dissolved in ethyl acetate and the insoluble material was filtered off. The organic layer, on dilution with hexane, deposited a solid which was collected by filtration and dried to afford estradiol (9) (0.75 g, 83%) The filtrate, on purification over a silica gel column, gave an additional amount of 2-trifluoroethoxy-6-oxoestra-1,3,5(10)-trien-3,17β-diol (9) (0.75 g, 83%): mp 186–188° C.; IR (KBr) 3400, 2940, 1660, 1600, 1505, 1440, 870 cm$^{-1}$, $^1$H NMR (DMSO-d$_6$+D$_2$O) δ 0.83 (s, 3 H), 1.20–2.85 (m, 13 H), 3.05 (bs, 1 H), 3.75 (t, J=8.5 Hz, 1 H), 4.58 (q. J=8.5 Hz, 2 H), 6.92 (s, 1 H), 7.63 (s, 1 H), 8.6 (s, 1 H). Anal. (C$_{20}$H$_{23}$F$_3$O$_4$) C, H.

EXAMPLE 7

2-Ethoxy-6-Hydroximinoestra-1,3,5(10)-Triene-3, 17β-Diol (11)

Sodium acetate (2.0 g, 30 mmol) was added to a stirred solution of 6-oxo derivative (10) (0.34 g, 1.03 mmol) in methanol (35 mL). Hydroxylamine hydrochloride salt (2.0 g, 29 mmol) in water (3 mL) was then added at room temperature. The resulting reaction mixture was stirred at 90° C. for 4 h. The solvent was removed under reduced pressure, the resulting residue was diluted with water (50 mL), and the product was extracted with ethyl acetate (3×150 mL). The combined organic layer was washed with water (100 mL), brine (100 mL), and dried over anhydrous sodium sulfate. The organic layer, on evaporation under reduced pressure, provided the crude product which was purified on a silica gel column using hexane-ethyl acetate mixture as eluant. Appropriate fractions were combined and evaporated under reduced pressure to afford hydroximino compound (11) (60–68%): mp 228–230° C.; IR (KBr) 3530, 3360–3140, 2930, 1605, 1505, 798, 870 cm$^{-1}$; $^1$H NMR (CDCl$_3$+DMSO-d$_6$+D$_2$O) δ 0.85 (s, 3 H), 1.10–2.45 (m, 13 H), 3.20 (dd, J=4.3 and 12.8 Hz, 1 H),3.75 (t, J=8.5 Hz, 1 H), 4.18 (q, J=8.5 Hz, 2 H) 6.80 (s, 1 H), 7.55 (s, 1 H). Anal. (C$_{20}$H$_{27}$NO$_4$) C, H.

EXAMPLE 8

2-(2',2', 2'-Trifluoroethoxy)-6-Hydroximino-Estra-1, 3,5(10)-Triene-3,17β-Diol (12)

Sodium acetate (2.86 g, 35 mmol) was added to a stirred solution of 6-oxo derivative (9) (0.45 g, 1.2 mmol) in methanol (55 mL). Hydroxylamine hydrochloride salt (2.2 g, 32 mmol) in water (3 mL) was then added at room temperature. The resulting mixture was stirred at 90° C. for 6 h. Then solvent was removed under reduced pressure, the resulting residue was diluted with water (60 mL), and product was extracted into ethyl acetate (3×120 mL). The combined organic layer was washed with water (70 mL), brine (70 mL), and dried over anhydrous sodium sulfate. The organic layer on evaporation under reduced pressure provided the crude product, which on crystallization from ethyl acetate-hexane mixture gave oxime (12) (0.3 g, 65%): mp 187–191° C.; IR (KBr) 3330, 2960–2860, 1500, 880, 750 cm$^{-1}$; $^1$H NMR (CDCl$_3$+DMSO-d$_6$+D$_2$O) δ 0.77 (s, 3 H), 1.10–2.38 (m, 11 H), 2.67 (s, 2 H), 3.05–3.27 (m, 2 H), 3.72 (t, J=8.5 Hz, 1 H), 4.50 (q, J=8.5 Hz, 2 H), 6.88 (s, 1 H), 7.57 (s, 1 H) 10.20 (s, 1 H). Anal. (C$_{20}$H$_{24}$NF$_3$O$_4$) C, H.

EXAMPLE 9

2-Ethoxy-6-Hydrazone-estra-1,3,5(10)-Triene-3, 17β-Diol (13)

Glacial acetic acid (0.5 mL) and anhydrous hydrazine (0.2 mL) were added under an argon atmosphere to a suspension of 6-oxo derivative (10) (0.4 g, 1.2 mmol) in anhydrous ethanol (25 mL). The resulting mixture was stirred at 95±5° C. After 2 h, anhydrous hydrazine (0.1 mL) was added to the reaction mixture, and the reaction was continued for 1 h. The solvent was removed under reduced pressure and the residue was diluted with water (25 mL). The aqueous solution was extracted with diclilromethane (3×100 mL). The combined organic layer was washed with water (100 mL) and dried over anhydrous sodium sulfate. The organic layer on evaporation under reduced pressure gave the desired hydrazone (13) (364 mg, 84%): mp 132–138° C.; R$_f$ 0.24 [ethyl acetate-hexane (4:1), silica gel] IR (KBr) 3370, 2960, 2860, 1610, 1570, 1500 cm$^{-1}$; $^1$H NMR (CDCl$_3$) δ 7.55 (s, 1 H), 6.78 (s, 1 H), 5.70 (bs, exchangeable with D$_2$O), 5.0 (bs exchangeable with D$_2$O), 4.15 (q, J=6.4 Hz, 2 H), 3.77 (dd, J=8.5 Hz, 1 H), 2.45–1.15 (m, 15 H), 0.8 (s, 3 H); MS m/z (relative intensity) 345 (MH$^+$), 330 (43), 263 (30), 243 (100), 202 (27), 189 (25), 165 (52); exact mass calcd. (MH)$^+$ 345.2178; found 345.2187. Anal. (C$_{20}$H$_{28}$N$_2$O$_3$.0.4CH$_2$Cl$_2$) C, H, N.

EXAMPLE 10

2-Ethoxyestra-1,3,5(10)-Triene-3,6α,17β-Triol (14)

Sodium borohydride (0.5 g, 13.2 mmol) was added under an argon atmosphere at room temperature to a solution of 6-oxo-derivative (10) (0.85 g, 2.57 mmol) in anhydrous methanol (30 mL). After completion (6 h), the solvent was evaporated under reduced pressure. The residue was dilu:ed with water (40 mL) and dichloromethane (170 mL), and then ice-cold 3N HCl (5 mL) was added. The dichloromethane layer was separated and the aqueous layer was extracted again with dichloromethane (150 mL). The combined organic layer was washed with water (50 mL), sodium bicarbonate (50 mL), and brine (50 mL) and dried over anhydrous sodium sulfate. The organic layer upon evaporation under reduced pressure followed by purification on a silica gel column provided a diastereomeric mixture of alcohols (0.5 g, 59%): mp 97–106, R$_f$ 0.27 [dichloromethane-methanol (95:5), silica gel]. Recrystallization from ethyl acetate gave a mixture enriched in 6-α diastereomer (14) (>95% 6-α isomer): IR (KBr) 3380, 2910, 2850, 1500, 1270, 1105, 1050, 870, 720 cm$^{-1}$; $^1$H NMR (CDCl$_3$) δ 7.12 (s, 1 H), 6.78 (s, 1 H), 5.65 (s, OH), 4.90–4.70 (bt, J=2.1 Hz, 1 H), 4.10 (q, J=6.4 Hz, 2 H), 3.75 (t, J=6.4 Hz, 1 H), 2.45–1.10 (m, 18 H), 0.8 (s, 3 H). Anal. (C$_{20}$H$_{28}$O$_4$.0.7H$_2$O): C, H.

EXAMPLE 11

2-Ethoxy-6-Tosylhydrazone-Estra-1,3,5(10)-Triene-3,17β-Diol (15)

Acetic acid (0.5 mL) was added to a stirred solution of 6-oxo derivative (10) (0.8 g, 2.42 mmol) in ethanol (30 mL). Tosylhydrazine (0.484 g 2.6 mmol) was added at room temperature. The resulting mixture was stirred at 90–95° C. for 5.5 h. More tosylhydrazine (0.2 g) was then added and heating continued for an additional 3.5 h. The solvent was then removed under reduced pressure, the resulting residue was diluted with water (50 mL), and the product was extracted with ethyl acetate (3×150 mL). The combined organic layer was washed with water (100 mL), brine (100 mL), and dried over anhydrous sodium sulfate. The organic layer on evaporation under reduced pressure provided an impure compound (15) which, on crystallization from an ethyl acetate-hexane mixture, gave pure compound (15) (0.6 g, 50%): mp 240° C., R$_f$ 0.24 [dichloromethane-methanol (95:1), silica gel]; IR (KBr) 3497, 3223, 2974–2939, 1621, 1592, 1577, 1499 cm$^{-1}$; $^1$H NMR (CDCl$_3$) δ 0.75 (s, 3 H), 1.15–2.38 (m, 16 H), 2.45 (s, 3 H), 2.65 (dd, J=4.3 and 17.2 Hz, 1 H), 3.72 (t, J=8.5 Hz, 1 H), 4.15 (q, J=6.4 Hz, 2 H), 5.60 (s, 1 H, OH), 6.73 (s, 1 H), 7.37 (d, J=8.5 Hz, 2 H), 7.57 (s, 1 H), 7.67 (s, 1 H), 7.95 (d, J=8.5 Hz, 2 H). Anal. (C$_{20}$H$_{27}$NO$_4$): C, H, N.

EXAMPLE 12

2-Ethoxy-6-(O-Methyl)hydroximino-Estra-1,3,5 (10)-Triene-3,17β-Diol (16)

A solution of methoxyamine (1.84 g) in distilled water (3.5 mL) was added to a suspension of 6-oxo-derivative (10) (0.33 g, 1 mmol) and anhydrous sodium acetate (1.94 g) in anhydrous MeOH (100 mL), and the resulting mixture was stirred at 95±5° C. for 4.5 h. The solvent was evaporated under reduced pressure. The residue was dissolved in water (50 mL) and the solution extracted with ethyl acetate (2×200 mL). The organic layer was washed with water (50 mL), brine (50 mL), and dried over anhydrous Na$_2$SO$_4$. The organic layer on evaporation gave an amorphous powder (0.32 g). The crude mixture was chromatographed over silica gel and eluted with hexane-ethyl acetate (1:1) to afford the desired product. This was further purified by crystallization from hexane-ethyl acetate to afford compound (16) (0.3 g, 83%): mp 92–97° C.; R$_f$ 0.56 (hexane-ethyl acetate (1:1), silica gel]; IR (KBr) 3460, 2960–2840, 1590, 1560, 1490, 1435, 890–872 cm$^{-1}$; $^1$H NMR (CDCl$_3$, 300 MHz) δ 7.55 (s, 1 H). 6.78 (s, 1 H), 5.5 (s, OH), 4.15 (q, 2 H), 3.97 (s, 3 H), 3.85–3.65 (m, 1 H), 3.05 (dd, J=8.5 and 21.4 Hz, 1 H), 2.45–1.15 (m, 16 H), 0.95 (t, J=8.5 Hz, 3 H), 0.8 (s, 3 H). Anal. (C$_{21}$H$_{29}$NO$_4$ 0.1 n-C$_6$H$_{12}$) C, H, N.

EXAMPLE 13

2-Ethoxy-3-Benzyloxy-Estra-1,3,5(10)-Triene-17β-Ol (17)

Benzyl bromide (4.5 g, 38 mmol) was added to a suspension of 2-ethoxy-β-estra-3,17β-diol (2) (4.5 g, 13 mmol) and potassium carbonate (8.6 g, 62 mmol) in anhydrous ethanol (100 mL) under argon atmosphere at 0° C. The resulting mixture was stirred at 100±5° C. for 7–8 h. The solvent was evaporated under reduced pressure and the residue was diluted with water, and the mixture was extracted with ethyl acetate (3×200 mL). The combined organic solution was washed with water (100 mL), sodium bicarbonate (120 mL), brine (100 mL), and dried over sodium sulfate. The ethyl acetate layer on evaporation under reduced pressure gave a viscous oil (5.8 g), which was used as such without any further purification in the next step: $^1$H NMR, (CDCl$_3$) δ 7.35 (s, 5 H), 6.75 (s, 1 H) 6.65 (s, 1 H), 5.5 (s, 1 H), 4.55 (s, 2 H), 4.04 (q, J=6.4, 2 H), 3.5 (t, J=8.5 Hz, 1 H), 2.75 (m, 3 H), 2.20–1.95 (m, 6 H), 1.90–1.80 (m, 2 H), 1.75–1.5 (m, 2 H), 1.45–1.1 (m, 7 H, 0.85 (s, 1 H).

EXAMPLE 14

2-Ethoxy-3-Benzyloxy-Estra-1,3,5(10)-Triene-17-One (18)

Benzyl bromide (4.5 g, 38 mmol) was added under argon atmosphere at 0° C. to a suspension of 2-ethoxy-β-estradiol (2) (4.5 g, 13 mmol) and potassium carbonate (8.6 g, 62 mmol) in anhydrous ethanol (100 mL). The resulting mixture was stirred at reflux for 7.5 h. The solvent was evaporated under reduced pressure, the residue was diluted with water, and the mixture was extracted with ethyl acetate (3×200 mL). The combined organic extract was washed with water (100 mL), sodium bicarbonate (120 mL), brine (100 mL) and dried over sodium sulfate. Evaporation of the ethyl acetate under reduced pressure gave a viscous oil containing (17), which was used without further purification. Activated MnO$_2$ (3 g) was added under an arcon atmosphere to a solution of crude alcohol (17) (1.6 g, 3.9 mmol) in anhydrous dichloromethane (50 mL). After 7 h, an additional amount of MnO$_2$ (5 g) was added and the reaction mixture was left over night at room temperature. MnO$_2$ (4 g) was added again and stirring was continued for 7 h. The mixture was filtered through a celite pad and the filtrate was evaporated under reduced pressure to give crude product, which was purified by column chromatography on silica gel using hexane, followed by hexane-CH$_2$C$_2$ (2:8) to afford pure ketone (18) (0.42 g, 8%): IR (neat) 3065, 2929, 2869, 2825, 1727, 1607, 1504, 1450 cm$^{-1}$; $^1$H NMR (CDCl$_3$) δ 0.92 (s, 3 H), 1.30–2.60 (m, 16 H), 2.83 (m, 2 H), 4.07 (q, J=8.5 Hz, 2 H), 5.10 (s, 2 H), 6.68 (s, 1 H), 6.88 (s, 1 H), 7.20–7.60 (m, 5 H).

EXAMPLE 15

2-Ethoxy-3-Benzyloxy-17β-Benzylaminoestra-1,3,5 (10)-Triene (19)

Glacial acetic acid (0.8 mL), benzylamine (1.6 mL, 15 mmol), and sodium cyanoborohydride (0.9 g, 14 mmol) were added under an argon atmosphere to a solution of 17-keto derivative (18) (2 g, 5 mmol) in anhydrous 1,2-dichloroethane (30 mL). The resulting mixture was stirred at room temperature for 72 h. Additional amounts of anhydrous benzylamine (0.4 mL), acetic acid (0.2 mL), and sodium cyanoborohydride (0.25 g) were added to the mixture, and stirring was continued for 24 h. The solvent was removed under reduced pressure, the residue was diluted with water (50 mL), and extracted with ethyl acetate (3×150 mL). The combined organic layer was washed with water (100 mL), sodium bicarbonate solution (100 mL), brine (100 mL), and dried over anhydrous sodium suleate. The organic layer on evaporation under reduced pressure gave crude product (3.1 g) which was subjected to column chromatography on silica gel using hexane, followed by hexane-CH$_2$Cl$_2$ (1:1), and finally CH$_2$Cl$_2$. Appropriate fractions were combined and evaporated under reduced pressure to give pure amine derivative (19) (2.2 G, 89%). The mp for aminederivative (19) could not be determined as it was a sticky solid which was used without any further purification: IR (KBr) 2921, 1608, 1508, 1453, 1264, 1209, 1119, 1019, 729 cm$^{-1}$; $^1$H NMR (CDCl3) δ 7.52–7.25 (m, 11 H), 6.85 (s, 1 H), 6.65 (s, 1 H), 4.20 (q, J=8.5 Hz, J=8.5 Hz, 2 H), 3.80 (s, 2 H) 2.75 (m, 1 H) 2.65 (t, J=8.5 Hz, 1 H), 2.35–2.12 (m, 4 H), 2.10 (s, 2 H), 1.85 (m, 4 H), 1.75–1.52 (m, 6 H), 1.40 (t, J=8.5, 3 H), 0.78 (s, 3 H).

EXAMPLE 16

2-Ethoxy-3-Hydroxy-17-α/β-Aminoestra-1,3,5(10)-Triene Hydrochloride (20)

20% Pd(OH)$_2$—C (1.7 g) was added carefully under argon atmosphere to a solution of 17-benzylamino derivative (29) (1.52 g, 3.0 mmol) in anhydrous THF (20–30 mL). The resulting mixture was hydrogenated at 45–50 psi on a Parr apparatus for 27 h. After completion, the catalyst was removed via filtration using a celite pad under argon atmosphere, and the pad was washed with THF (150 mL), followed by a 1:1 mixture of THF-CH$_2$Cl$_2$ (100 mL). The filtrate obtained on evaporation under reduced pressure gave impure compound (1.08 g), which was purified by col-imn chromatography. The resulting material was then converted to the hydrochloride salt (0.16 g, 15%) by dissolving it in ether and then bubbling HCl gas through the solution: mp 270° C.; IR (KBr) 3137, 2931–2261, 1612, 1499, 1396 cm$^{-1}$; $^1$H NMR (CDCl$_3$) δ 8.60 (bs, exchangeable with D$_2$O), 8.20 (bs, exchangeable with D$_2$O), 6.75 (s, 1 H), 6.52 (s, 1 H), 3.95 (q, J=8.5 Hz, 2 H), 3.60–3.20 (m, 4 H), 3.00 (t, J=8.5 Hz, 1 H), 2.82–2.42 (m, 4 H), 2.40–1.90 (m, 4H), 1.88–1.55 (m, 3 H), 1.27 (t, J=8.5, 3 H), 0.78 (s, 3 H). Anal. (C$_{20}$H$_{30}$ClNO$_2$.0.5C$_2$H$_5$OH) C, H, N.

EXAMPLE 17

Tubulin Assays

Electrophoretically homogeneous tubulin was purified from bovine brain as described previously (Hamel et al., *Biochemistry* 23:4173–4184 (1984)). Determination of IC$_{50}$ values for the polymerization of purified tubulin was performed as described in detail elsewhere (D'Amato et al. *Proc. Natl. Acad. Sci. U.S.A.* 91:3964–3968 (1994)). In brief, tubulin was preincubated at 26° C. with varying compound concentrations, reaction mixtures were chilled on ice, GTP (required for the polymerization reaction) was added, and polymerization was followed at 26° C. by turbidimetry at 350 nm in Gilford recording spectrophotometers equipped with electronic temperature controllers. Four instruments were used, and two control reaction mixtures were present in each experiment. The extent of polymerization after a 20 min incubation was determined (the values for the two controls were usually within 5% of each other). IC$_{50}$ values were determined graphically. Active compounds were examined in at least three independent assays, while inactive compounds (defined as IC$_{50}$ value>40 μM) were examined in at least two independent experiments. Inhibition of colchicine binding to tubulin was performed as described previously (D. Amato et al., *Proc. Natl. Acad. Sci. U.S.A.* 91:3964–3963 (1994)). Reaction mixtures contained 1.0 μM tubulin (0.1 mg/mL), 5.0 μM [$^3$H]colchicine, and 50 μM inhibitor. Incubation was for 30 min at 37° C.

The inhibitory activities of 2-methoxy estradiol (1), 2-ethoxy estradiol (2), and the new analogs on tubulin polymerization are reported in Table 1. Inhibition of tubulin polymerization was investigated using electrophoretically homogeneous tubulin from bovine brain. 2-ethoxy estradiol (2) was over three times more active than 2-methoxy estradiol (1). In addition, a number of the new analogs showed significant activity (IC$_{50}$≦5.0 μM). Six of the new analogs were more potent than 2-methoxy estradiol (1) (IC$_{50}$ 2.9 μM), and three of them proved to be more potent then 2-ethoxy estradiol (2) (IC$_{50}$ 0.91 μM). The most potent of the new compounds was 6-oximino-2',2',2-trifluoroethoxyestradiol (12), which displayed an IC$_{50}$ of 0.5 μM for inhibition of tubulin polymerization. The potency of (12) was followed closely by the corresponding 2-ethoxy analog (11) (IC$_{50}$ 0.62 μM), ancdthen the oxime ether (16) (IC$_{50}$ 0.75 μM)

EXAMPLE 18

Activity of 2-Alkoxy Estradiols an Analogs Thereof in the National Cancer Institute Anticancer Screen The effects of the analogs on cancer cell growth was investigated in the National Cancer Institute (NCI) Developmental Therapeutics Program's in vitro panel of approximately 55 cell lines (Grever et al., *Seminars in Oncology* 19:622 (1992), Alley et al., *Cancer Research* 48:589 (1988) and Montes et al., *J. National Cancer Institute* 83:757 (1991)). Representative results are listed in Table 1 for HOP-62 non-small-cell lung cancer cells, HCT-116 colon cancer cells, SF-539 central nervous system (CNS) cancer cells, UACC-62 melanoma cells, OVCAR ovarian cancer cells, SN12-C renal cancer cells, DU-145 prostate cancer cells, and MDA-MB-435 breast cancer cells.

TABLE 1

Cytotoxicities and Antitubulin Activities of 2-Methoxyestradiol and Analog

| No. | Lung HOP-62 | Colon HCT-116 | CNS SF-539 | Melanoma UACC-62 | Ovarian OVCAR | Renal SN12-C | Prostate DU-145 | Breast MDA-MB-435 | MGM[b] | Inhibn of Tubulin Polymn IC$_{50}$ (IC$_{50}$ μM) |
|---|---|---|---|---|---|---|---|---|---|---|
| 1 | 0.70 | 0.47 | 0.32 | 0.36 | 0.21 | 0.95 | 1.8 | 0.080 | 1.30 | 2.9 ± 0.6 |
| 3 | 11.6 | 3.22 | 1.38 | 2.32 | 0.46 | 4.46 | 7.05 | 0.28 | 2.63 | 1.7 |
| 2 | 0.018 | 0.026 | 0.014 | 0.016 | 0.016 | 0.039 | 0.065 | <0.01 | 0.076 | 0.91 ± 0.5 |
| 7 | 20.0 | 21.1 | 22.6 | 17.7 | 23.7 | 19.8 | 19.8 | 18.4 | 19.5 | >40 |
| 6 | 8.70 | 3.71 | 5.11 | 3.33 | 3.52 | 23.5 | 15.0 | 26.5 | 9.77 | 6.0 |
| 10 | 0.03 | 0.02 | 0.71 | 0.01 | 0.63 | 0.18 | 0.17 | <0.01 | 0.13 | 4.8 |
| 11 | <0.01 | <0.01 | — | <0.01 | <0.01 | <0.01 | <0.01 | <0.01 | 0.04 | 0.62 |
| 12 | <0.01 | <0.01 | <0.01 | <0.01 | <0.01 | — | <0.01 | <0.01 | 0.01 | 0.5 |
| 13 | 1.18 | 2.12 | 2.76 | 0.88 | 5.43 | 16.8 | 17.0 | 6.50 | 4.17 | 15 |
| 14 | — | 0.35 | — | 0.28 | 0.35 | 0.66 | 0.71 | 5.39 | 0.83 | 2.5 |
| 15 | 5.14 | 6.67 | 3.45 | — | 3.18 | 12.1 | 14.9 | 0.92 | 6.16 | >40 |
| 16 | <0.01 | <0.01 | — | <0.01 | <0.01 | 0.26 | 0.32 | 0.02 | 0.24 | 0.75 |
| 20 | 10.9 | 3.15 | 3.99 | 3.61 | 1.25 | 5.24 | 1.93 | 1.74 | 3.31 | >40 |

[a]The cytotoxicity GI$_{50}$ values are the concentrations corresponding to 50% growth inhibition.
[b]Mean graph midpoint for all human cancer cell lines (approximately 55) tested.

It is evident from these cytotoxicity results that the two most potent inhibitors of tubulin polymerization, oximes (11) and (12), are extremely potent as cytotoxic agents, with GI$_{50}$ values consistently less than 10$^{-8}$ molar, the lowest concentration normally investigated in the screen.

These results are further emphasized in Table 2, which is a more complete listing of the data available for oxime (12), the most potent member of the series. In all of the cell lines tested, compound (12) displayed $GI_{50}$ values of less than $10^{-8}$ molar. The dose-response "curves" for (12) and the other very potent members of this series were typically "flat" lines showing maximum cytotoxicity down to the lowest concentrations tested. In addition, it is evident that there is a general correlation of cytotoxicity with inhibition of tubulin polymerization, which supports the hypothesis that inhibition of tubulin polymerization is responsible for the cytotoxic activities of the compounds in this series.

TABLE 2

Cytotoxicities of Oxime 12

| Panel/Cell Line | $Log_{10}GI_{50}(M)$ |
|---|---|
| Leukemia | |
| CCRF-CEM | <−8.00 |
| HL-60(TB) | <−8.00 |
| K562 | <−8.00 |
| MOLT-4 | <−8.00 |
| RPMI-8226 | <−8.00 |
| SR | <−8.00 |
| Non-Small Cell Lung Cancer | |
| A549/ATCC | <−8.00 |
| EKVX | <−8.00 |
| HOP-62 | <−8.00 |
| NCI-H23 | <−8.00 |
| NCI-H322M | <−8.00 |
| NCI-H460 | <−8.00 |
| NCIH-522 | <−8.00 |
| Colon Cancer | |
| HCT-116 | <−8.00 |
| HTC-15 | <−8.00 |
| SW-260 | <−8.00 |
| CNS Cancer | |
| SF-295 | <−8.00 |
| SF-539 | <−8.00 |
| SNB-19 | <−8.00 |
| SNB-75 | <−8.00 |
| U251 | <−8.00 |
| Melanoma | |
| LOX IMVI | <−8.00 |
| M14 | <−8.00 |
| SK-MEL-28 | <−8.00 |
| SK-MEL-5 | <−8.00 |
| UACC-62 | <−8.00 |
| Ovarian Cancer | |
| OVCAR-3 | <−8.00 |
| OVCAR-8 | <−8.00 |
| Renal Cancer | |
| 786-0 | <−8.00 |
| ACHN | <−8.00 |
| RXF 393 | <−8.00 |
| UO-31 | <−8.00 |
| Prostate Cancer | |
| DU-145 | <−8.00 |
| Breast Cancer | |
| MCF7 | <−8.00 |
| MCF7/ADR-RES | <−8.00 |
| HS 578T | <−8.00 |
| MDA-MB-435 | <−8.00 |
| MDA-N | <−8.00 |
| BT-549 | <−8.00 |
| Average (all cell lines) | <−8.00 |

EXAMPLE 19

Estrogen Binding Affinity Assay

One potential concern about the present series of tubulin polymerization inhibitors is that they might have some affinity for estrogen receptors and therefore poesess either estrogenic activity or be estrogen antagonists, thus complicating their application as anticancer agents. In order to address this potential problem, the relative estrogen receptor binding affinities of the most potent analogs (11), (12), and (16) were investigated. For comparison purposes, the relative estrogen receptor binding affinities of 2-methoxy estradiol and 2-ethoxy estradiol (2) were also determined. Comparative radiometric binding assays were employed using rat uterine cytosol at 0° C. to determine the relative binding affinities (RBA) as compared to estradiol (RBA=100, $K_{id}$= 0.3 nM) according to procedures described in Katzenellenbogen et al., *Biochemistry* 12:7985 (1973). By definition, estradiol is given an RBA value of 100. The assay of (11), (12) and (16) were conducted at 0° C. for 20 hours, while those for (1) and (2) were performed at 0° C. for 18 hours. The coefficient of variation in replicate experiments is typically less than 30%.

The results are listed in Table 3. Both 2-ethoxy-6-oximinoestradiol (11) and 2-ethoxy-6-methoximinoestradiol (16) had no affinity for the estrogen receptor within the limits of the assay (RBA<0.001), while 2-(2',2',2'-trifluoroethoxy)-6-oximinoestradiol (12) displayed very week affinity for the receptor (RBA=0.0007). Each of the next analogs had much lower affinity for the estrogen receptor than either 2-methoxy estradiol (RBA=0.245) or 2-ethoxy estradiol (12) (RBA=0.011). These results make it clear that estrogen receptor binding will not be a factor in the potential therapeutic application of the most potent of the present tubulin polymerization inhibitors, (11), (12) and (16).

| Compound | $RBA^a$(0° C.) |
|---|---|
| (1) | 0.245 |
| (2) | 0.011 |
| (11) | <0.001 |
| (12) | 0.007 |
| (16) | <0.001 |

In conclusion, an array of new estradiol analogs has been synthesized in an effort to improve on the anticancer and antitubulin activities of 2-methoxy estradiol (1) and to further decrease their affinity for the estrogen receptor. These objectives have been realized in the four most potent of the new compounds 2-ethoxy estradiol (2), (11), (12), and (16).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the claims.

What is claimed is:

1. A compound represented by the following structural formula:

wherein:

$R_1$ is a lower alkyl group or substituted lower alkyl group;

$R_2$ is —OH or —$NH_2$; and $R_3$ is selected from the group consisting of =O, =N—$NH_2$, =N—NH—$SO_2$-(lower alkyl), =N—NH—$SO_2$-(substituted lower alkyl), =N—NH—$SO_2$-phenyl, =N—NH—$SO_2$-(substituted phenyl), =N—OH, and =N—O—$CH_3$, with the proviso that $R_3$ is not =O if $R_1$ is methyl and $R_2$ is —OH.

2. The compound of claim 1 wherein:

$R_1$ is ethyl or 2,2,2-trifluoroethyl;

$R_2$ is —OH and has the beta configuration; and $R_3$ is =N—OH, or =N—O—$CH_3$.

3. A compound represented by the following structural formula:

* * * * *